United States Patent
Yamada

(10) Patent No.: US 10,278,613 B2
(45) Date of Patent: May 7, 2019

(54) IMAGE PROCESSING APPARATUS, IMAGE PROCESSING METHOD, AND A NON-TRANSITORY COMPUTER READABLE RECORDING MEDIUM CONTAINING AN IMAGE PROCESSING PROGRAM

(71) Applicant: FUJIFILM Corporation, Tokyo (JP)

(72) Inventor: Kenta Yamada, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 720 days.

(21) Appl. No.: 14/747,635

(22) Filed: Jun. 23, 2015

(65) Prior Publication Data

US 2015/0282887 A1    Oct. 8, 2015

Related U.S. Application Data

(63) Continuation of application No. PCT/JP2013/007401, filed on Dec. 17, 2013.

(30) Foreign Application Priority Data

Dec. 25, 2012 (JP) ................ 2012-280943

(51) Int. Cl.
| | | |
|---|---|---|
| *A61B 5/05* | (2006.01) | |
| *A61B 5/055* | (2006.01) | |
| *G06T 19/00* | (2011.01) | |
| *A61B 1/00* | (2006.01) | |
| *A61B 34/10* | (2016.01) | |

(Continued)

(52) U.S. Cl.
CPC .......... *A61B 5/055* (2013.01); *A61B 1/00009* (2013.01); *A61B 34/10* (2016.02); *G06T 19/003* (2013.01); *A61B 1/2676* (2013.01); *A61B 6/032* (2013.01); *A61B 6/5217* (2013.01);

(Continued)

(58) Field of Classification Search
None
See application file for complete search history.

(56) References Cited

U.S. PATENT DOCUMENTS

| | | | |
|---|---|---|---|
| 2008/0183073 A1* | 7/2008 | Higgins | ............... G06T 19/003 600/425 |
| 2008/0234700 A1 | 9/2008 | Trovato et al. | |
| 2015/0257847 A1 | 9/2015 | Higgins et al. | |

FOREIGN PATENT DOCUMENTS

| | | |
|---|---|---|
| JP | 2008-29694 A | 2/2008 |
| JP | 2009-56143 A | 3/2009 |

(Continued)

OTHER PUBLICATIONS

Communication dated Apr. 19, 2016 from Japanese Patent Office in counterpart Application No. 2012-280943.

(Continued)

*Primary Examiner* — Patricia J Park
(74) *Attorney, Agent, or Firm* — Sughrue Mion, PLLC

(57) ABSTRACT

Extracting a tubular structure from volume data, determining a target region which should be reached by an endoscope through the tubular structure, extracting, among plurality on a route of the tubular structure, a point that satisfies a given condition as a target point that should be reached by a distal end portion of the endoscope, and identifying and determining a route of the tubular structure from a predetermined start point in the tubular structure to the extracted target point as a route through which the endoscope should be passed.

14 Claims, 5 Drawing Sheets

(51) Int. Cl.
    *A61B 1/267*    (2006.01)
    *A61B 6/03*     (2006.01)
    *A61B 6/00*     (2006.01)
(52) U.S. Cl.
    CPC ..... *A61B 2034/107* (2016.02); *A61B 2576/02* (2013.01); *G06T 2210/41* (2013.01)

(56)            References Cited

FOREIGN PATENT DOCUMENTS

JP      2009-511155 A      3/2009
JP      2009-542374 A     12/2009
JP      2010-517633 A      5/2010
JP      2010-220742 A     10/2010
JP      2012-200403 A     10/2012
WO    WO 2008096376 A1 *  8/2008   ........... G01C 21/005

OTHER PUBLICATIONS

International Search Report for PCT/JP2013/007401 dated Apr. 28, 2014.

* cited by examiner

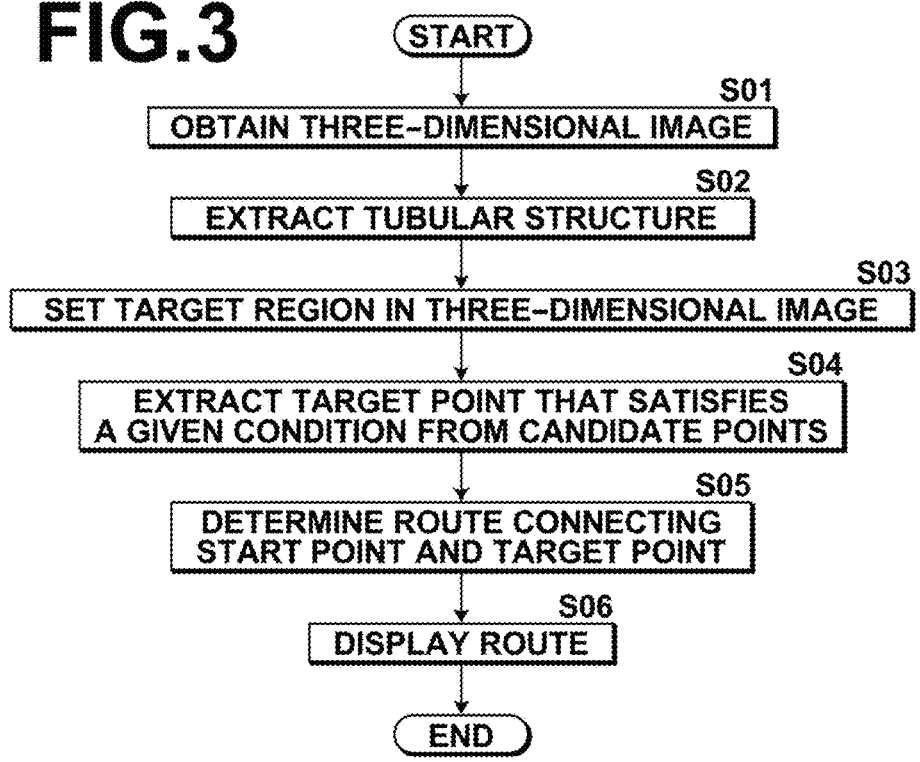
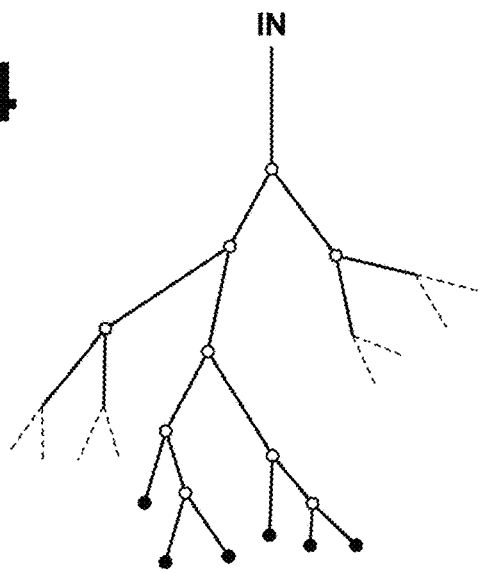

IMAGE PROCESSING APPARATUS, IMAGE PROCESSING METHOD, AND A NON-TRANSITORY COMPUTER READABLE RECORDING MEDIUM CONTAINING AN IMAGE PROCESSING PROGRAM

CROSS-REFERENCE TO RELATED APPLICATIONS

This application is a Continuation of PCT International Application No. PCT/JP2013/007401 filed on Dec. 17, 2013, which claims priority under 35 U.S.C. § 119 (a) to Japanese Patent Application No. 2012-280943 filed on Dec. 25, 2012. Each of the above applications is hereby expressly incorporated by reference, in its entirety, into the present application.

BACKGROUND OF THE INVENTION

Technical Field

The present invention relates to an image processing apparatus, image processing method, and image processing program for extracting an insertion route of an endoscope into a tube of a body, such as a tubular structure composed of a trachea and bronchi, using a three-dimensional image.

Background Art

Recently, image-based diagnosis has been performed widely in the medical front and an affected area is diagnosed using three-dimensional image data (volume image data) of a subject captured, for example, by an X-ray computed tomography (CT) system. For example, a three-dimensional image of a tubular structure composed of a trachea and bronchi may be generated by performing volume rendering on the volume data obtained by imaging a chest region. The three-dimensional image of the tubular structure is used to three-dimensionally identify the position of an abnormal region suspicious of, for example, lung cancer, and a bronchial endoscope is inserted to the position of the abnormal region to observe or treat the abnormal region, or otherwise various procedures are performed, such as collecting a tissue sample using, for example, biopsy forceps.

But, it is not easy to lead the distal end of an endoscope through a tube branched in multiple stages like a bronchus to an abnormal region located close to the end of the bronchus. Therefore, before inserting the endoscope into a tubular structure composed of a trachea and bronchi, it is preferable that the position of the abnormal region is confirmed, then a target point where a distal end portion of the endoscope should be located for performing a desired access to the abnormal region is set, and a route to the target point is set in advance based on a three-dimensional image of the tubular structure. To support the determination of such an endoscope route, a method is proposed in which a three-dimensional image of bronchi is generated based on volume data and a route from the lower respiratory tract to the target region along a tube is extracted on the three-dimensional image as described, for example, in Japanese Unexamined Patent Publication No. 2009-056143 and PCT Japanese Publication No. 2009-511155.

Further, as a guide to determine a route for a bronchoscope to safely reach the affected area, a technique is proposed in which a score is calculated for each region of bronchi based on various aspects, including route length, respiratory tract diameter, joint angle between respiratory tracts as described, for example, in PCT Japanese Publication No. 2009-542374.

SUMMARY OF THE INVENTION

Here, if the distal end portion of the endoscope is tilted largely inside the tubular structure from the direction of the route of the tubular structure to direct the distal end portion of the endoscope to the target region from the route of the tubular structure, the inner wall of the tubular structure may possibly be pressed by the distal end portion of the endoscope inside the tubular structure which is undesirable from the viewpoint of reducing burden on the tubular structure. But, the use of the end points of the routes determined by the methods disclosed in Japanese Unexamined Patent Publication No. 2009-056143, PCT Japanese Publication No. 2009-511155, and PCT Japanese Publication No. 2009-542374 as the target point may sometimes cause the target region to be located in a direction largely different from the direction of the route when positioning the distal end portion of the endoscope at the target point and performing a desired access, and, in such a case, the distal end portion of the endoscope needs to be tilted largely from the direction of the route of the tubular structure.

The present invention has been developed in view of the circumstances described above, and it is an object of the present invention to provide an image processing apparatus, operation method thereof, and image processing program capable of determining a route of a tubular structure by appropriately extracting a target point on the route of the tubular structure of a subject to be treated or observed by an endoscope such that the burden on the tubular structure caused by largely tilting a distal end portion of the endoscope inside the tubular structure from a direction of the route of the tubular structure is reduced.

An image processing apparatus of the present invention includes a tubular structure extraction unit that extracts, from volume data captured by imaging a region of a subject which includes a tree-shaped tubular structure, the tubular structure, a target region setting unit that determines a target region which should be reached by an endoscope through the tubular structure in the volume data, a target point extraction unit that extracts, among points on a route of the tubular structure, a point that satisfies a first condition that the point on the route is located within a given range from the target region and a second condition that a judgement angle, which is an angle formed between a direction from the point on the route toward the target region and a direction in which the route of the tubular structure extends from the point on the route, is less than or equal to a reference angle which is at least a given acute angle, as a target point that should be reached by a distal end portion of the endoscope, and a route determination unit that identifies and determines a route of the tubular structure from a predetermined start point in the tubular structure to the extracted target point as a route through which the endoscope should be passed.

An image processing method to be performed by the foregoing image processing apparatus of the present invention includes a tubular structure extraction step that extracts, from volume data captured by imaging a region of a subject which includes a tree-shaped tubular structure, the tubular structure, a target region setting step that determines a target region which should be reached by an endoscope through the tubular structure in the volume data, a target point extraction step that extracts, among points on a route of the tubular structure, a point that satisfies a first condition that the point on the route is located within a given range from the target region and a second condition that a judgement angle, which is an angle formed between a direction from the point on the route toward the target region and a direction in which the route of the tubular structure extends from the point on the route, is less than or equal to a reference angle which is at least a given acute angle, as a target point that should be reached by a distal end portion of the endoscope, and a route determination step that identifies and determines a route of the tubular structure from a predetermined start point in the tubular structure to the extracted target point as a route through which the endoscope should be passed.

An image processing program of the present invention causes a computer to perform the foregoing image processing method.

In the present invention, "tubular structure" may be any structure of a subject which can be represented as a tree structure, and typically the tubular structure is preferably composed of a trachea and bronchi.

In the present invention, "route of the tubular structure" is a route passing through a lumen of the tubular structure that serves as the route through which the endoscope moves in the tubular structure. For example, a core line of the tubular structure may be taken as the route of the tubular structure.

In the present invention, "point on the route is located within a given range from the target region" refers to that the distance between the point on the route and a point in the target region is within a given range. The point in the target region used to calculates the distance may be set arbitrarily as long as it is in the target region. The given range may be set arbitrarily according to the type of the endoscope used, the treatment method, and the size of the target region. For example, in a case where the purpose is to resect the target region, the given range is preferably set such that the entire target region is included in the range reachable by a treatment tool from a distal end portion of the endoscope. In a case where the purpose is to observe or medicate the target region, or to collect a sample from the target region, the given range is preferably set such that at least a portion of the target region is included in the range reachable by the treatment tool from the distal end portion of the endoscope. Therefore, the point in the target region used to calculate the distance may be a point in the target region located closest to the point on the route, a point in the target region located farthest from the point on the route, or the center of gravity or the center of the target region.

The term "a direction from the point on the route toward the target region" refers to a direction from the point on the route toward a given point in the target region. The given point used to calculate the "direction from the point on the route toward the target region" may be any point as long as it is in the target region. For example, the given point used to calculate the "direction from the point on the route toward the target region" may be the center of gravity or the center of the target region, a point of the target region that forms a largest judgement angle, or a point of the target region that forms a smallest judgement angle, or a point specified by a manual operation of a user.

The term "a direction in which the route of the tubular structure extends from the point on the route" refers to a direction away from the start point of the tubular structure along the route of the tubular structure at the point on the route.

The "reference angle" may be set to any angle that can sufficiently reduce the burden on the tubular structure caused by tilting a distal end portion of the endoscope from the route direction within an acute angle range. Further, a plurality of reference angles may be provided according to an arbitrary condition.

For example, in the image processing apparatus according to the present invention, the second condition is preferably changed in the reference angle according to the diameter of the tubular structure such that the smaller the diameter of the tubular structure, the smaller the reference angle.

In the foregoing case, if the diameter of the tubular structure is greater than or equal to the diameter of the endoscope multiplied, by a given factor which is greater than or equal to 1, a first reference angle is used as the reference angle, while if the diameter of the tubular structure is smaller than the diameter of the endoscope multiplied by the given factor, a second reference angle which is smaller than the first reference angle is used as the reference angle. In this case, the given factor may be any value as long as it is greater than or equal to 1. For example, the given factor is preferably a value that causes the outer diameter of the endoscope to be almost equal to the inner diameter of the tubular structure. The given factor is preferably in the range of 1 to 1.5, more preferably in the range of 1 to 1.3, and preferably in the range of 1 to 1.1 and may be in the range of 1 to 1.05. In the foregoing case, for example, the first reference angle and the second reference angle may be set arbitrarily as long as they can sufficiently reduce the burden on the tubular structure caused by tilting the endoscope distal end portion from the route of the tubular structure and the second reference angle is smaller than the first reference angle. For example, the second reference angle is preferably less than or equal to an angle 2.5 degrees greater than a half angle of view of the endoscope, and the second reference angle is preferably less than or equal to the half angle of view of the endoscope. In this case, the first reference angle may be less than or equal to an angle 5 degrees greater than the half angle of view.

The target point extraction unit preferably takes the target point as a point further satisfies a third condition that the diameter of a portion of the tubular structure where the point is located is less than a given threshold value. For example, in a case of a tubular structure composed of a trachea and bronchi (hereinafter, referred to as "trachea structure"), the given threshold value is preferably the diameter of the trachea or a major bronchus which are the regions where damage should be avoided.

Further, the target point extraction unit preferably takes the target point as a point further satisfies a fourth condition that a portion of the tubular structure where the point is located does not belong to a given portion of the tubular structure where damage should be avoided. For example, in a case of a trachea structure, the given portion is preferably the trachea or a major bronchus where damage should be avoided.

Still further, the target point extraction unit preferably takes the target point as a point further satisfies a fifth condition that there is no obstacle between the point and the target region. For example, in a case of the trachea structure, a condition that no interlobar membrane, which is a region where damage should be avoided, is present as an obstacle between the target point and the target region.

Further, the target point extraction unit preferably identifies, among a plurality of divided sections of the tubular structure, a section closest to the target region and extracts the target point only in the identified section.

According to the image processing apparatus, image processing method, and image processing program, from volume data captured by imaging a region of a subject which includes a tree-shaped tubular structure, the tubular structure is extracted, a target region which should be reached by an endoscope through the tubular structure is determined in the volume data, among points on a route of the tubular structure, a point that satisfies a first condition that the point on the route is located within a given range from the target region and a second condition that a judgement angle, which is an angle formed between a direction from the point on the route toward the target region and a direction in which the route of the tubular structure extends from the point on the route, is less than or equal to a reference angle which is at least a given acute angle, is extracted as a target point that should be reached by a distal end portion of the endoscope, and a route of the tubular structure from a predetermined start point in the tubular structure to the extracted target point is identified and determined as a route through which the endoscope should be passed. Therefore, a target point may be extracted so as to be located within the given range from the target region based on the first condition and such that at least a portion of the target region is included within the reference angle range from the route direction, and positioning of a distal end portion of the endoscope at the determined target point allows a successful access to the target region, because the target region is within the given range from the target region, and the burden on the tubular structure of the subject caused by tilting the distal end portion of the endoscope inside the tubular structure from the route direction of the tubular structure to be reduced.

BRIEF DESCRIPTION OF THE DRAWINGS

FIG. 3 is a flowchart illustrating a flow of processing of an image processing method according to an embodiment of the present invention.

FIG. 4 illustrates an example of a tree structure of a tubular structure.

DESCRIPTION OF EMBODIMENTS

Figure 1:
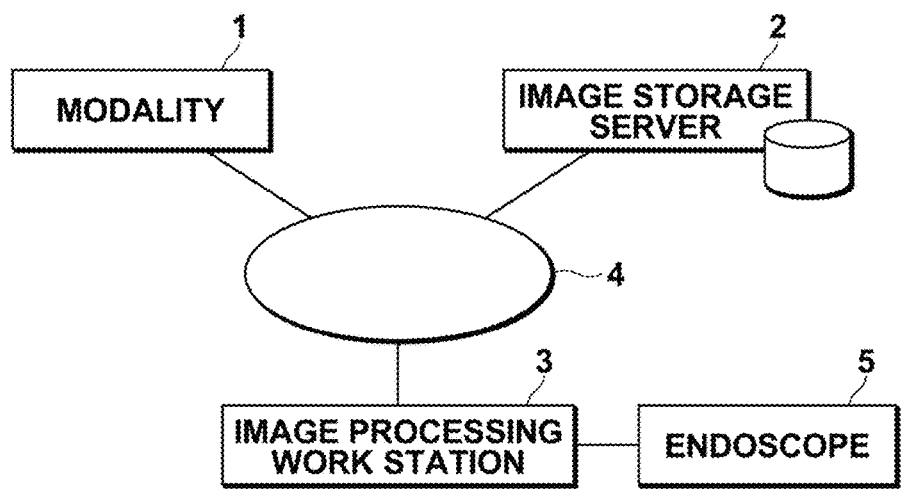
FIG. 1 is a schematic configuration diagram of a medical system which includes an image processing apparatus according to an embodiment of the present invention.

Hereinafter, an embodiment of the image processing apparatus of the present invention will be described in detail with reference to the accompanying drawings. FIG. 1 is a schematic configuration diagram of a medical system which includes an image processing apparatus according to an embodiment of the present invention. The medical system includes a modality 1, an image storage server 2, an image processing workstation 3, a network 4, and an endoscope 5.

The modality 1 includes a system that images a diagnostic target region of a patient to generate three-dimensional medical image data representing the subject, and outputs the image data with auxiliary information defined by the Digital Imaging and Communications in Medicine (DICOM) standard attached thereto. Specific examples may include a CT system, a MRI system, and the like.

The image storage server 2 is a computer that stores, in an image database, and manages medical image data obtained by the modality 1 and image data subjected to image processing in the workstation 3, and includes a large capacity external storage device and database management software. The three-dimensional medical image data captured in the modality 1 are stored as volume data V.

The image processing workstation 3 has a known hardware configuration, including, for example, a CPU, a main memory, an auxiliary storage device, an input/output interface, a communication interface, an input unit (mouse, keyboard, and the like) 37, a display monitor 38, and a data bus, and a known operating system and the like are installed. A graphical user interface (GUI) (not shown) is implemented in the image processing workstation 3 and a user may obtain desired medical image data from the modality 1 or from the image storage server 2, as well as inputting various instructions through the GUI. Further, the workstation 3 has a function to perform various image processing on the obtained medial image data and to display a generated image on a display device.

The image processing workstation 3 functions as the image processing apparatus of the present invention when image processing is implemented by installing an image processing program. The image processing program is distributed by being stored in a storage medium, such as a CD-ROM or through a network, such as the Internet, and installed on the computer.

The network 4 connects each system of the modality 1, the image storage server 2, and the image processing workstation 3. The communication between each system via the network 4 is performed based on the DICOM or a similar protocol.

Figure 2:
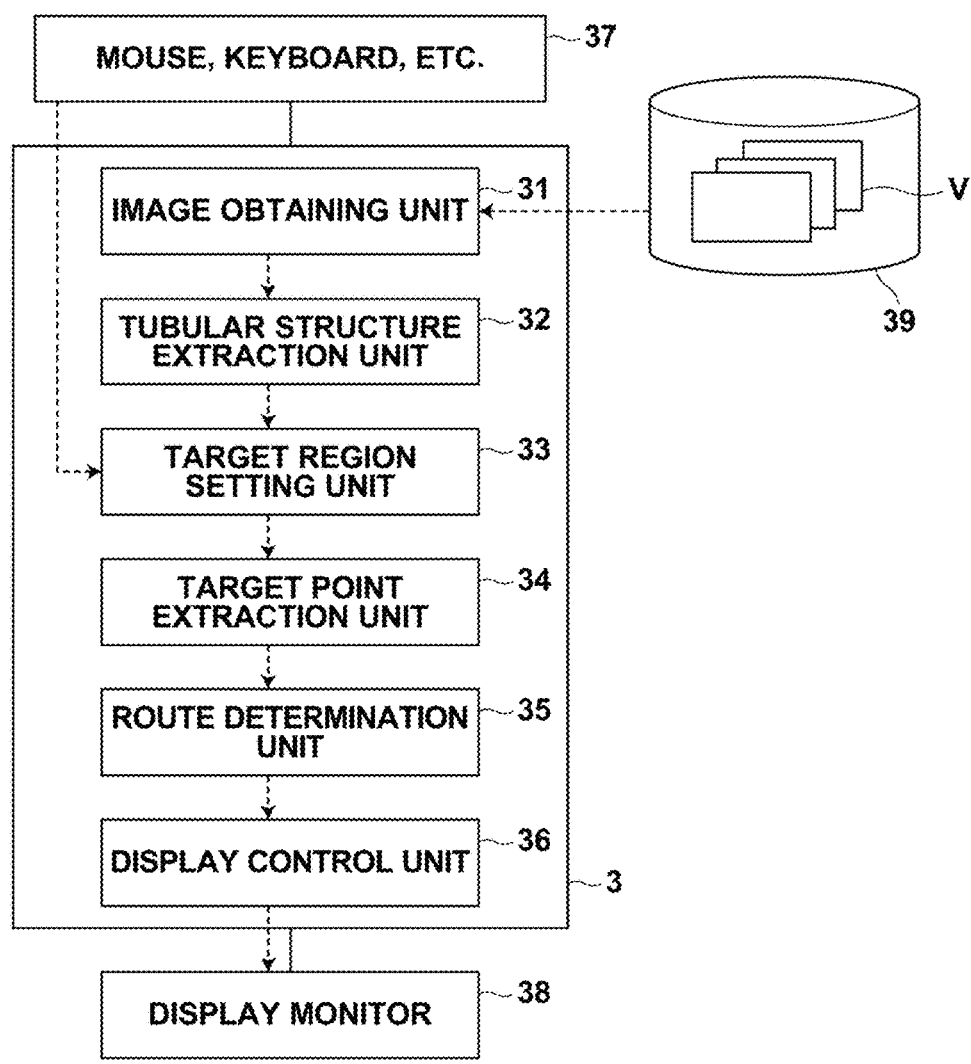
FIG. 2 is a block diagram of an image processing apparatus according to an embodiment of the present invention, illustrating a configuration thereof.

FIG. 2 is a block diagram of some of the functions of the image processing workstation 3 related to the image processing apparatus 3 according to an embodiment of the present invention. As shown in the drawing, the image processing apparatus 3 according to an embodiment of the present invention includes an image obtaining unit 31 that obtains volume data V captured by imaging a region of a subject which includes a tree-shaped tubular structure, from the storage unit 39, the image storage server 2, or the like to the memory, a tubular structure extraction unit 32 that extracts the tubular structure from the volume data V captured by imaging the region of the subject which includes the tubular structure, a target region setting unit 33 that determines a target region which should be reached by an endoscope through the tubular structure in the volume data V, a target point extraction unit 34 that extracts, among points on a route of the tubular structure, a point that satisfies a predetermined condition as a target point which should be reached by a distal end portion of the endoscope, a route determination unit 35 that identifies and determines a route of the tubular structure from a predetermined start point in the tubular structure to the extracted target point as a route through which the endoscope should be passed, and a display control unit 36 that displays an image obtained by each processing on the display, as appropriate.

FIG. 3 is a flowchart illustrating a flow of an image processing method according to the present embodiment. With reference to FIG. 3, a method for determining a route for inserting an endoscope in a trachea structure using the image processing method according to an embodiment of the present invention will be described.

First, volume data V captured by a CT system (modality 1) by imaging a chest region of a patient (subject) to be examined are stored in the image storage server 2. In order to simulate the insertion of an endoscope into a trachea structure, the operator operates an operation terminal interface of a known ordering system installed in the image processing workstation 3 to make a request for obtaining volume data V of a patient to be examined. In response to this operation, the image processing workstation 3 transmits a search request to the image storage server 2 for the volume data V, and the image storage server 2 obtains the volume data V of the patient through a database search and transmits the obtained volume data V to the image processing workstation 3. The image processing workstation 3 stores the volume data V transmitted from the image storage server 2 in the storage unit 39 (S01).

Next, in response to a user instruction, the image processing software is activated in the image processing workstation 3 and processing for extracting an endoscope insertion route from the entrance of the trachea structure to the target region is started.

First, the tubular structure extraction unit 32 extracts the structure of the trachea structure of the patient from the volume data V (S02). The trachea structure is considered to appear in the volume data V in the following manner. That is, the inside of the trachea structure appears on a CT image as an area having relatively low CT values (pixel values) because the pixels inside the trachea structure correspond to the air area but the wall of the trachea structure is considered to be a cylindrical structure or a line (tubular) structure having relatively high CT values. Therefore, the trachea structure is extracted by performing structural analysis of shape based on the distribution of CT values with respect to each pixel. Here, Hessian analysis is performed to identify a main axis direction of the trachea structure based on a pixel value of each pixel, thereby extracting the trachea and bronchial structure using the same method as that described in Japanese Unexamined Patent Publication No. 2012-200403, which is a prior application of the present applicant (for more detailed information, refer to Japanese Unexamined Patent Publication No. 2012-200403 or Japanese Unexamined Patent Publication No. 2010-220742 filed by the present applicant, and the like).

Note that the tubular structure extraction unit 32 may extract the tubular structure by any method as long as it is capable of extracting a tubular structure. In the present embodiment, the tubular structure extraction unit 32 obtains the center line of the trachea and bronchial structure as the route of the trachea structure, and further obtains a diameter of the trachea or a bronchus with respect to each position on the center line of the trachea structure and stores them associated with each other. Further, the tubular structure extraction unit 32 extracts an interlobar membrane from the volume data V by a known method and stores information that identifies the extracted interlobar membrane.

Then, the extracted tree structure is classified into a start point, an end point, a tree structure branch point, an edge, and the start point IN, end points, and tree structure branch points are connected by edges (sides), whereby tree structure data T representing the trachea structure consisting of a trachea and bronchi are obtained. Characteristic amounts, such as the diameter of the trachea or a bronchus at each position of the tree structure, and the length of each edge (length between bifurcations of bronchi) are stored as the tree structure data T, as required. FIG. 4 illustrates an example of a tree structure. In FIG. 4, a branch point, an end point, and an edge are represented by a white circle, a black circle, and a line respectively.

Next, the target region setting unit 33 receives an input indicating the position of the target region R. For example, a volume rendering image M representing a tubular structure generated from the volume data V is displayed on the screen of the display monitor of the image processing workstation 3 and the position (center and size) of a target region R (refer to FIG. 5) is inputted by encircling the position of a lung tumor with the mouse on the displayed image (S03). Then, the target region setting unit 33 obtains the inputted position and sets the target region R. Further, the target region setting unit 33 obtains the position of each pixel belonging to the set target region R by a known method and stores them in a memory, and further calculates a coordinate of the center of gravity of the target region R based on the position of each pixel and stores it in the memory.

Figure 5:
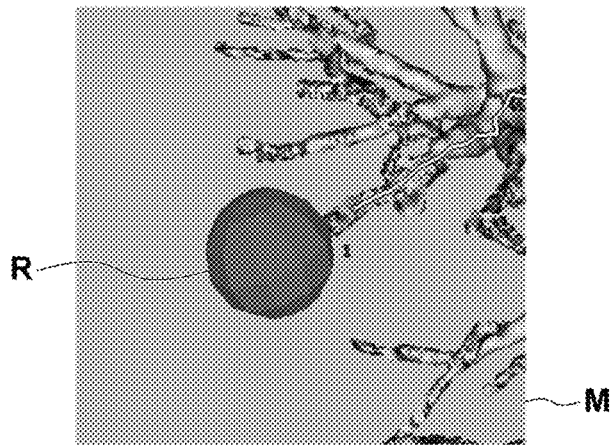
FIG. 5 illustrates an example of a pseudo three-dimensional image of a tubular structure.

In the present embodiment, the display control unit 36 displays the extracted bronchial area and the target region R on the volume rendering image M in a superimposing manner to confirm the selected target region R, as illustrated in FIG. 5. Preferably, the display control unit 36 displays the bronchial area as a pseudo three-dimensional image, like the volume rendering image, for selecting the target region R, and may further display a desired image, such as a cross-sectional image of bronchi, with the pseudo three-dimensional image in a comparable manner.

Next, the target point extraction unit 34 sets n candidate points Pi ($0 \leq i < n$) on the center line of the route of the tubular structure at an equal interval. Then, the target point extraction unit 34 extracts, among the candidate points Pi ($0 \leq i < n$) on the center line of the route of the tubular structure, a candidate point that satisfies conditions (1) to (4) below as a target point P which should be reached by the distal end of the endoscope (904).

(1) The candidate point Pi is located within a given range L from the target region R.

(2) The judgement angle θ, which is an angle formed between a direction from the candidate point Pi toward the target region R and a direction in which the route of the tubular structure extends from the candidate point Pi, is less than or equal to a reference angle which is at least a given acute angle.

(3) There is no obstacle between the candidate point Pi and the target region R.

(4) The diameter of a portion of the tubular structure where the candidate point Pi is located is less than a given threshold value.

The condition (1) is provided for setting the target point P within a given range L from the target region R. Since the target point P is the point for positioning a distal end portion of an endoscope to perform, for example, observation or treatment of the target region R, the target point is preferably determined at a place near the target region R where the distal end portion of the endoscope may perform the observation or treatment of the target region R. Therefore, the given range L may be set arbitrarily according to the type of the endoscope used, the treatment method, and the size of the target region within a range that allows the distal end portion of the endoscope to achieve the purpose, such as the observation or treatment of the target region R. For example, in a case where the purpose is to resect the target region R, the given range is preferably set such that the entire target region R is included in the range reachable by a treatment tool from the distal end portion of the endoscope. For example, it is conceivable that the condition (1) is set such that the distance from the candidate point Pi to the farthest point in the target region R is less than or equal to a given distance which is a maximum distance that the treatment tool can be extended. In a case where the purpose is to observe or medicate the target region R, or to collect a sample from the target region R, the given range is preferably set such that at least a portion of the target region R is included in the range reachable by a treatment tool from the distal end portion of the endoscope. For example, it is conceivable that the condition (1) is set such that the distance from the candidate point Pi to the nearest point in the target region R is less than or equal to a given distance which is a maximum distance that the treatment tool can be extended.

In the present embodiment, a judgement is made with respect to the condition (1) by whether or not a distance Li between the target region R and the candidate point Pi is less than or equal to the given range L. Further, in a case where a plurality of points that satisfy the condition (1) is found, the target point extraction unit 34 extracts in order from the candidate point Pi shortest to a point in the target region R among candidate points P0 to PN on the route, in the present embodiment.

Figure 6:
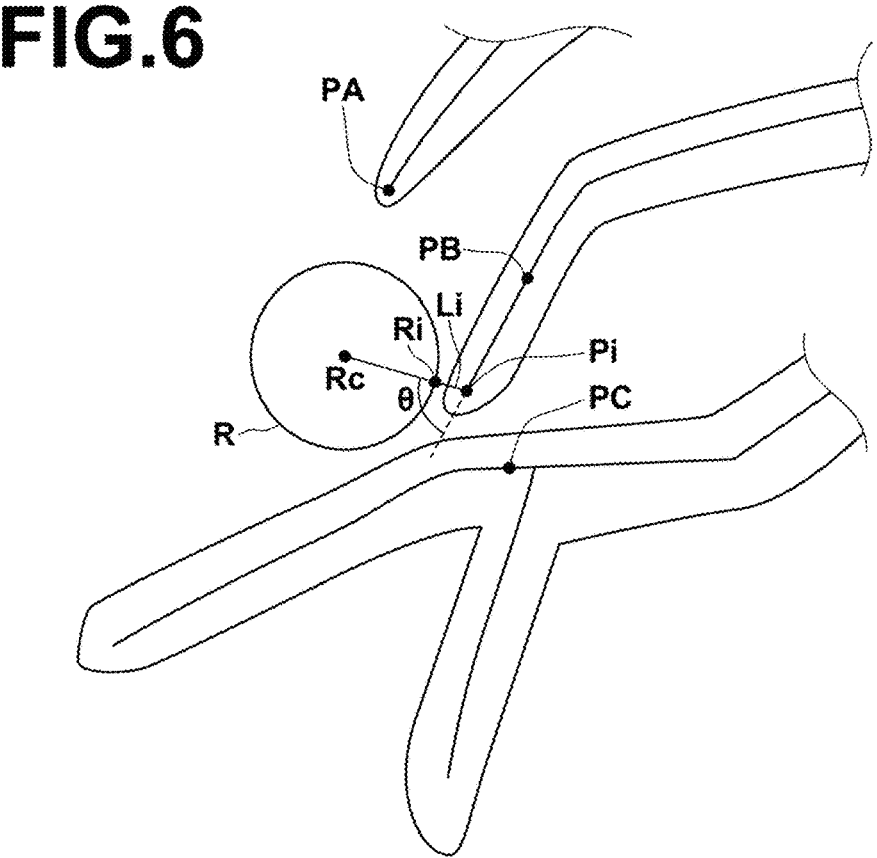
FIG. 6 is a drawing for explaining a method for determining whether or not a candidate point satisfies conditions (1) and (2).

FIG. 6 is a drawing for explaining a judgement method with respect the condition (1). Note that the position and size of a target region R, and the shape of the tubular structure are simplified in FIG. 6 for the purpose of explanation, and the dispositions and sizes of the branches of the tubular structure are changed, as appropriate, from those of FIG. 5. A pixel of those included in the target region R having a shortest distance to the candidate point Pi is indicated as Ri in FIG. 6. As illustrated in FIG. 6, in the present embodiment, the given range L is set such that the shortest distance Li between the target region R and the candidate point Pi is less than or equal to the given range L. Further, the given range L is set to a length longer than a maximum reachable length Lmax of the treatment tool (maximum length that the treatment tool can extend from the distal end of the endoscope). Setting the given range L longer than or equal to the maximum reachable length Lmax of the treatment tool, as described above, allows the target point P to be extracted such that at least a portion of the target region R is reachable by the treatment tool.

Further, not limited to the foregoing embodiment, the condition (1) may be set such that the largest distance between the target region R and the candidate point Pi is less than or equal to the given range L. Preferably, the given range L is set to a length longer than or equal to the maximum reachable length Lmax of the treatment tool and, in this case, it is highly likely that the treatment tool may suitably reach the entire target region R. That identical effect may be obtained by determining the given range L by an arbitrary method capable of determining the given range L to a distance that allows the distal end portion of the endoscope to reach the entire target region R.

The condition (2) is provided for setting the target point P at a position where it is not necessary to tilt the distal end portion of the endoscope largely with respect to the route (position where it is not necessary to tilt the distal end portion of the endoscope at least greater than or equal to a right angle with respect to the direction of the route) when accessing the target region R from the target point P.

In the condition (2), "a direction from a point on the route toward the target region" refers to a direction from a point on the route toward a given point in the target region, and the given point in the target region may be any point as long as it is located in the target region. Further, "a direction in which the route of the tubular structure extends from a point on the route" refers to a direction away from the start point of the tubular structure along the route of the tubular structure (direction away from the origin of the tree structure). In the present embodiment, a given point in a target region is set to the center of gravity RC of the target region and, the angle at each candidate point Pi between a vector from Pi toward the center of gravity RC and a tangent vector toward a direction in which the route extends at each candidate point Pi is taken as the judgement angle θ, as illustrated in FIG. 6.

In the present embodiment, the reference angle is changed according to the diameter of the tubular structure, such that the smaller the diameter of the tubular structure, the smaller the judgment angle, in the condition (2). In a tree-shaped tubular structure, the smaller the diameter of a tubular structure, like a bronchus, the smaller the gap between the endoscope and the tubular structure, and, therefore, it is considered that the burden on the tubular structure caused by tilting the endoscope distal end portion largely with respect to the route of the tubular structure is increased as the diameter of the tubular structure is reduced. Therefore, it is considered to be preferable to reduce the tilt of the endoscope distal end portion with respect to the direction of the route of the tubular structure, as the diameter of the tubular structure is reduced. The change in the different reference angle according to the diameter of the tubular structure such that the smaller the diameter of the tubular structure, the smaller the reference angle, allows the target point P to be set while satisfactorily reducing the burden on the tubular structure caused by the inner wall of the tubular structure being pressed by the endoscope.

Preferably, an inner diameter of the tubular structure is used as the diameter of the tubular structure in the condition (2), because the gap between the distal end portion of the endoscope and the inner wall of the tubular structure may be represented more accurately.

The "reference angle" may be set to any angle within an acute angle range according to the purpose, as long as it can sufficiently reduce the burden on the tubular structure caused by bending the endoscope distal end portion. Further, a plurality of reference angles may be provided according to an arbitrary condition.

For example, in the condition (2), it is preferable that a first reference angle is used as the reference angle in a case where the diameter of the tubular structure is greater than or equal to the diameter of the endoscope multiplied by a given factor, which is greater than or equal to 1, and the diameter of the tubular structure is considered to be substantially the same as that of the endoscope, while a second reference angle smaller than the first reference angle is used as the reference angle in a case where the diameter of the tubular structure is smaller than the diameter of the endoscope multiplied by the given factor.

In the present embodiment, when the half angle of view of the endoscope is taken as w, the judgement angle θ in the condition (2) is assumed to be less than or equal to a first reference angle θ1 (=ω+5°) in a case where the inner diameter of the tubular structure is greater than or equal to 1.05 times the diameter of the endoscope distal end portion, while the judgement angle θ in the condition (2) is assumed to be less than or equal to a second reference angle θ2 (=ω) in a case where the inner diameter of the tubular structure is smaller than 1.05 times the diameter of the endoscope distal end portion. Further, it is possible to switch the second reference angle θ2 to θ2'=ω+2.5° by receiving a user input.

As described above, in a case where the diameter of the tubular structure is smaller than the diameter of the endoscope multiplied by the given factor and the diameter of the tubular structure is considered to be substantially the same as that of the endoscope, the use of the half angle of view ω of the endoscope as the second reference angle θ2 allows the target region R to be included in the field of view of the endoscope without tilting the endoscope distal end portion at the target point.

Further, if it is known that the endoscope distal end portion is allowed to be tilted by an angle θk with respect to the direction of the route because of the characteristics of the tubular structure, such as flexibility, it is preferable that the allowable angle θk is used to set the second reference angle as the sum of the allowable angle θk (2.5 degrees, here) and the half angle of view ω. In this case, when accessing the target region R from the target point P, the target point P may be set such that the endoscope distal end portion can access the target region within an angle range in which the endoscope distal end portion can be tilted reasonably from the route by appropriately reflecting the angle allowed for the endoscope distal end portion to tilt with respect to the route of the tubular structure.

Also, in a case where the diameter of the tubular structure is greater than or equal to the diameter of the endoscope multiplied by the given factor and the diameter of the tubular structure is considered to be sufficiently larger than the diameter of the endoscope, if it is known that the endoscope distal end portion is allowed to be tilted by an angle θk1 with respect to the direction of the route according to the diameter of the tubular structure, it is preferable that the allowable angle θk1 is used to set the first reference angle as the sum of the half angle of view ω and the allowable angle θk1 (5 degrees, here). In this case also, the target point P may be set such that the endoscope distal end portion can access the target region within an angle range in which the endoscope distal end portion can be tilted reasonably from the route by appropriately reflecting the angle allowed for the endoscope distal end portion to tilt with respect to the route of the tubular structure.

The given factor of the condition (2) is not limited to the present embodiment and any value may be used as long as it causes the diameter of the tubular structure to be considered as substantially the same as that of the endo scope and is greater than or equal to 1. For example, the given factor is preferably in the range of 1 to 1.5, more preferably in the range of 1 to 1.2, and may be in the range of 1 to 1.1.

In a case, for example, where the target region R is resected, the reference angle is preferably set such that the entire target region R is included in an angle range reachable by the treatment tool to allow the treatment tool to reach the entire target region R. As the treatment tool is considered to extend to almost the same direction as the optical direction of the endoscope distal end portion, for example, it is preferable that, in the condition (2), a maximum angle formed between a direction in which the route of the tubular structure extends and a direction from the target point P toward a point in the target region R is set as the judgement angle θ, and the reference angle is set to less than or equal to a known angle θk2 in which the endoscope distal end portion is allowed to be tilted with respect to the direction of the route. Further, even in a case where such allowable angle cannot be obtained, for example, the reference angle is preferably less than or equal to 60 degrees and more preferably less than or equal to 45 degrees, since it is considered to be preferable that the tilt angle of the endoscope distal end portion with respect to the direction of the route is small. In this way, when the endoscope distal end portion is positioned at the target point, if the condition (2) is set such that the reference angle becomes small, the endoscope distal end portion may access the target region R from the target point while maintaining the tilt of the endoscope distal end portion from the route of the tubular structure to small.

In the foregoing embodiment, the use of the ratio between the diameter of endoscope and the diameter of the tubular structure in determining the reference angle allows the gap between the inner wall of a tubular structure and the endoscope inside the tubular structure to be reflected appropriately in the condition (2). Further, the use of a diameter of the endoscope distal end portion as the diameter of endoscope is preferable because it allows the gap between the inner wall of a tubular structure and the endoscope inside the tubular structure to be reflected more accurately.

The condition (3) is provided for setting the target point P at a position where no obstacle is found that interferes with the observation or treatment of the target region R when accessing from the target point P to the target region R. In the present embodiment, if an interlobar membrane is present between a candidate point Pi and the target region R, the candidate point Pi is determined not to satisfy the condition (3), while if no interlobar membrane is present between a candidate point Pi and the target region R, the candidate point Pi is determined to satisfy the condition (3). The method of judging the condition (3) is not limited to the present embodiment and any known method capable of judging the presence or absence of an obstacle may be used. For example, an obstacle judgement may be made by the method described in Japanese unexamined Patent Publication No. 2008-029694.

The condition (4) is provided for setting the target point P at a position other than a route portion where setting of a target point P is desired to be avoided for various reasons, such as avoiding damage. The present embodiment utilizes the nature of a tree-shaped tubular structure, like bronchi, that the diameter is gradually reduced toward an end portion from the origin of the tree structure and identifies a desired tubular structure portion where setting of a target point P is desired to be avoided (excluded portion) by the diameter of the excluded portion, and the condition (4) is set such that no target point P is set in a tubular structure portion which is equal, in diameter, to the excluded portion. The present embodiment uses an average diameter of major bronchi as the upper limit of the tubular structure portion at a target point P to allows the target point P to be set at a route portion having a diameter less than or equal to the upper limit, whereby a target point P may be set at a position other than the excluded portion, such as the trachea and a major bronchus where damage is desired to be avoided (setting of a target point P is desired to be avoided).

The condition (4) may use the diameter of the endoscope as the lower limit of the diameter of the tubular structure portion at the target point P to make it impossible to set the target point P at a route portion having a diameter smaller than the diameter of the endoscope. In this case, the target point P may be set at a position other than a thin bronchial portion into which the endoscope cannot be inserted. Further, both the upper and lower limits may be proved for the diameter of the tubular structure portion at the target point P.

Next, the target point extraction unit 34 calculates a judgement angle θ at a candidate point Pi and makes a judgement with respect to the condition (2). As illustrated in FIG. 6, the judgement angle θ is calculated as an angle between the vector extending from the candidate point Pi toward the center of gravity RC of the target region R and the vector parallel to the tangent line at the candidate point Pi and extending toward the direction in which the tubular structure extends.

The target point extraction unit 34 obtains a diameter of the portion of the tubular structure where the candidate point Pi is located, and if the diameter of the tubular structure is greater than or equal to 1.05 times the diameter of the endoscope, determines whether or not the judgement angle θ is less than or equal to the first reference angle θ1, while if the diameter of the tubular structure is smaller than 1.05 times the diameter of the endoscope, determines whether or not the judgement angle θ is less than or equal to the second reference angle θ2. Then, if the judgement angle θ at the candidate point Pi is less than or equal to the first reference angle θ1 or the second reference angle θ2, the candidate point Pi is determined to satisfy the condition (2). Then, if the candidate point Pi is determined to satisfy the condition (2), a determination is made whether or not the candidate point Pi satisfies the condition (3). Then, if the candidate point Pi is determined to satisfy the condition (3), a determination is made whether or not the candidate point Pi satisfies the condition (4).

If the candidate point Pi does not satisfy any one of the conditions (1) to (4), the target point extraction unit 34 terminates the determination of the candidate point Pi with respect to the conditions (1) to (4), and repeats the determination with respect to the conditions (1) to (4) for a remaining candidate point for which no determination has been made with respect to the conditions (1) to (4) in the manner as described above. Then, if a candidate point Pi that satisfies all of the conditions (1) to (4) is extracted, the candidate point Pi is extracted as the target point P. In the present embodiment, the target point extraction unit 34 is configured to extract a given number of target points P and extracts a candidate point Pi that satisfies the foregoing conditions (1) to (4) until a given number of three target points are extracted. Hereinafter, the extracted three target points are referred to as PA, PB, and PC in order in which they are extracted. Here, a description will be made on the assumption that the target points PA, PB, and PC are extracted from different branches with each other, but the target points PA, PB, and PC may be extracted as being located in the same branch.

In this way, if a candidate point Pi having a shortest distance to the target region R is extracted as the point that satisfies the condition (1) and, among those that satisfy the condition (1), a candidate point that satisfies other conditions (the conditions (2) to (4), here) is extracted as a target point, the target point P may be determined at a position as close to the target region R as possible, and when the distal end portion of the endoscope is positioned at the target point P, the target point R may be accessed appropriately. The present embodiment extracts a candidate point Pi located closest to the target region R as a point that satisfies the condition (1). Therefore, candidate points Pi that satisfy the conditions (2) to (4) are extracted in ascending order of distance to the target region R, and the distance to the target points PA, PB, and PC increases in this order.

The route determination unit 35 identifies and determines a route of the tubular structure from a given start point to the extracted target point as the route through which the endoscope should be passed (S05).

Here, the route determination unit 35 extracts a plurality of typical routes for a virtual endoscope to reach the target region R through the tubes from the entrance IN of bronchi based on the tree structure data T. In a case where the target region R has a certain size, like a tumor, target points PA, PB, and PC on different branches are extracted in the vicinity of the target region R and with respect to each target point PA, PB, and PC, a plurality of routes from the entrance of the bronchi to the target point R, may possibly present. The route determination unit 35 obtains target points PA, PB, and PC in the tree structure data T corresponding to those on the routes of bronchi connecting the target region R and searches routes from the start point IN of the tree structure data T corresponding to the entrance of bronchi to the target points PA, PB, and PC based on the tree structure data T. Note that the conventionally practiced various route search methods may be used for the route searching.

Figure 7:
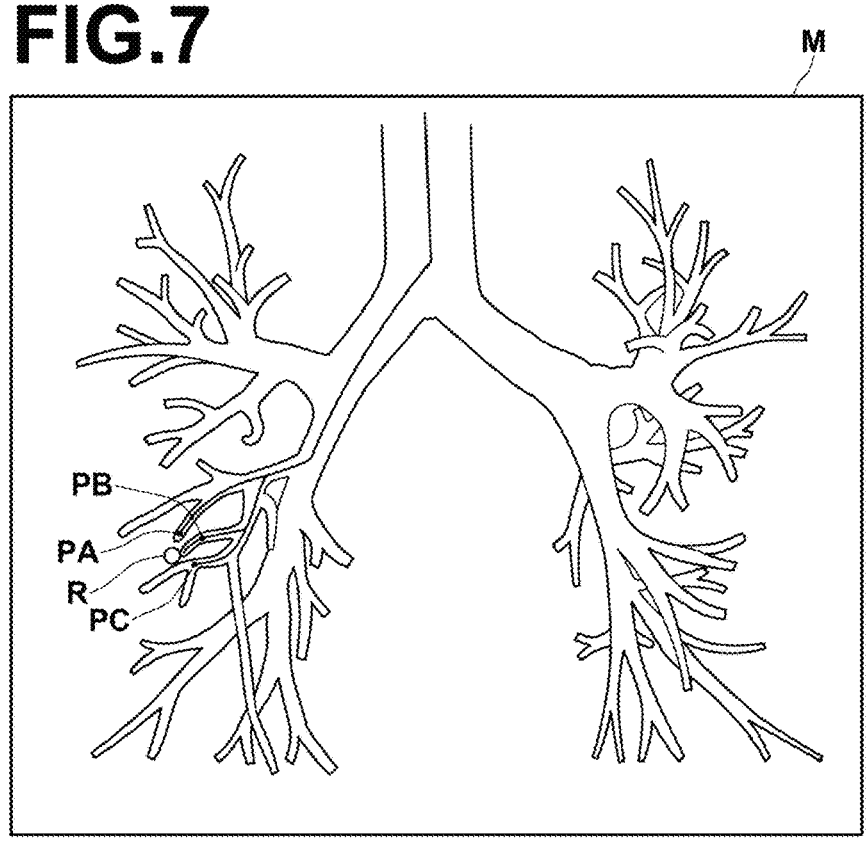
FIG. 7 illustrates an example of a route connecting a start point and a target point of a tubular structure.
Figure 8:
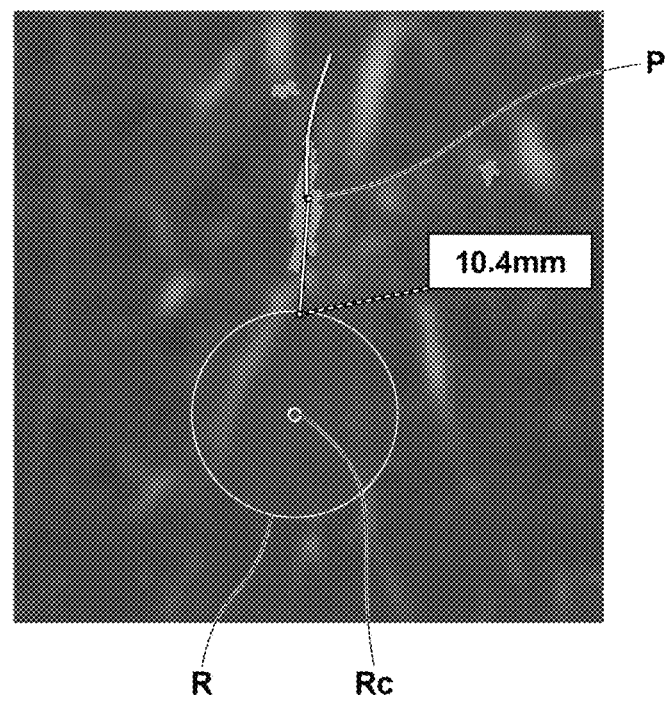
FIG. 8 illustrates an example of an extracted target point and a target region.

The display control unit 36 generates a trachea structure rendering image obtained through volume rendering the trachea and bronchi based on the bronchial tree structure data T and the generated image is referred to as a trachea structure rendering image M. Then, the determined routes are superimposed on the trachea structure rendering image M, as illustrated in FIG. 7 (S06). FIG. 7 illustrates an example of the trachea structure rendering image M and FIG. 8 shows an image superimposing a target point P and a target region R on a tomographic image. The target point P shown in FIG. 8 is preferably extracted such that, when a distal end portion of an endoscope is positioned at the target point P, a treatment tool can access the target point R appropriately by extending the treatment tool from the target point P in the direction in which the route extends.

As described above, according to the present embodiment, a target point may be determined within a range near the target region R that allows an easy access to the target region R by determining the target point so as to satisfy the condition (1). Further, when positioning the endoscope distal end portion and accessing the target region R, a tilt angle of the endoscope distal end portion with respect to the route of the tubular structure may be maintained at least at an acute angle by determining the target point so as to satisfy the condition (2). Therefore, determining the target point so as to satisfy both of the conditions (1) and (2) and positioning the endoscope distal end portion at the determined target point allow the burden on the tubular structure caused by tilting the distal end portion of the endoscope with respect to the route to perform desired access to the target region R.

For example, no conventional method extracts the target point such that the burden on the tubular structure caused by tilting the endoscope distal end portion with respect to the route is reduced, as in the condition (2). Therefore it has happened, for example, that the candidate point Pi located closest to the target region R in FIG. 6 is extracted as the target point. But, if the endoscope distal end portion is positioned at the candidate point Pi in FIG. 6, it is necessary to tilt the endoscope distal end portion almost at right angle with respect to the direction in which the route extends to direct the endoscope distal end portion, for example, toward the center of gravity of the target region R for observation or treatment, so that it is highly likely that the tubular structure incurs a heavy burden. As the present embodiment extracts a target point so as to satisfy the condition (2), positioning of the endoscope distal end portion at any of points PA, PB, and PC allows the target point R to be captured within the field of view of the endoscope and desired access, such as collecting a sample from the target region R, to be performed while maintaining the direction of the endoscope distal end portion within an angle range in which the endoscope distal end portion is allowed to be tilted inside the tubular structure.

Further, as a target point can be determined such that an obstacle that blocks the view and hinders treatment is avoided by determining the target point so as to satisfy the condition (3), the observation and treatment of the target region may be performed appropriately by the endoscope from the determined target point.

Still further, as a target point may be extracted at a position other than a tubular structure portion where setting of a target point P is desired to be avoided by determining the target point so as to satisfy the condition (4), a safer route may be set. Note that any method other than the method of the condition (4) may be used as long as it is capable of determining the target point such that a given tubular structure portion where damage should be avoided is excluded.

For example, the target point extraction unit 34 may use a condition (5) or a condition (6) below, instead of the condition (4).

(5) The tubular structure portion where the candidate point Pi is located does not belong to a given tubular structure portion where damage should be avoided.

(6) The wall thickness of the tubular structure portion where a candidate point Pi is located is within a given range.

In the foregoing embodiment, if a trachea and a major bronchus are set in the condition (5) as the given portion where setting of a target point P is desired to be avoided, a target point P may be set at a position other than a route portion where setting of a target point is desired to be avoided, as in the condition (4).

In a case where the condition (5) is used, the tubular structure extraction unit 32 stores the extracted tubular structure by dividing the tubular structure into a plurality of sections by a known method, such as the method of comparing the extracted tubular structure to a model structure of a known tubular structure. Then, it is conceivable that, based on the specific section to be excluded stored in advance, the target point extraction unit 34 extracts a target point P, among the plurality of sections, only in the sections of the route of the tubular structure other than the specific section in the condition (5).

In the foregoing embodiment, an arrangement may be adopted in which the target point extraction unit 34 obtains a wall thickness of the tubular structure portion where a candidate point Pi is located and the condition (6) is used instead of the condition (4). It is conceivable that a desired tubular structure portion where setting of a target point P is desired to be avoided (excluded portion) is identified by the wall thickness of the excluded portion utilizing the nature of a tree-shaped tubular structure, like bronchi, that the wall thickness is gradually reduced toward an end portion from the origin of the tree structure and the condition (6) is set such that no target point P is set in a tubular structure portion which is equal, in wall thickness, to the excluded portion. For example, an average wall thickness of major bronchi is used as the upper limit of the tubular structure portion at the target point P to allow a target point P to be set at a route portion having a wall thickness less than or equal to the upper limit, whereby a target point P may be set at a position other than the excluded portion, such as the trachea and major bronchi where damage is desired to be avoided (setting of a target point P is desired to be avoided), as in the condition (4).

Further, the target point extraction unit 34 may set any condition as the condition for extracting a target point. For example, all of the conditions (1) to (6), any one of the conditions (1) to (6), or any combination of one or more conditions arbitrarily selected from the conditions (1) to (6) may be used, or a target point may be extracted by further combining a condition other than the foregoing conditions. Still further, each condition may be used in any order for making determinations. Further, only one target point or a plurality of target points may be extracted.

In the foregoing embodiment, the target point extraction unit 34 may identify a section closest to the target region R among a plurality of divided sections of the tubular structure and a target point may be extracted only in the identified section. Such arrangement is preferable since calculation load and time can be reduced.

In the foregoing case, the tubular structure extraction unit 32 may divide the tubular structure by any method of dividing a tubular structure. For example, if the tubular structure is a trachea structure, the trachea structure may be divided into three sections: major bronchi; a bronchial area included in the right lung (other than the major bronchi); and a bronchial area included in the left lung (other than the major bronchi). Otherwise, a bronchial area included in each of the upper lobe, middle lobe, lower lobe of the right lung, upper lobe, and lower lobe of the left lung may be taken as one section.

Further, the target point extraction unit 34 may be configured to extract a plurality of target points and to calculate scores for the plurality of target points based on any arbitrary condition that allows a judgment to be made whether or not the target points are preferable points for positioning the distal end portion of the endoscope, and the target points may be prioritized based on the scores. For example, based on a plurality of viewpoints, like the foregoing conditions (1) to (6), target points may be prioritized such that the shorter the distance between the target region R and the target point P, the higher the priority. Otherwise, scores may be calculated by various known methods, such as a method that prioritizes target points such that the smaller the judgement angle, the higher the priority, and a plurality of calculated scores is weight added and the target points P may be prioritized based on the added score.

For example, an arrangement may be adopted in the foregoing embodiment in which candidate points Pi having as smaller judgment angles θ as possible are extracted as points that satisfy the condition (2) and among the points that satisfy the condition (2), those that satisfy other conditions (for example, the conditions (1), (3), and (4)) are extracted as target points P by a given number, and the target points P are prioritized in the ascending order of the judgment angle. In this case, when the distal end portion of the endoscope is positioned at the target point P, the tilt of the endoscope distal end portion from the route to direct the endoscope distal end portion toward the target region R may be reduced satisfactorily, and the burden on the tubular structure of the subject caused by tilting the endoscope distal end portion inside the tubular structure may be reduced satisfactorily.

Further, in a case where different routes are obtained respectively for a plurality of target points, the route determination unit 35 may calculate scores for the routes based on any arbitrary condition that allows a judgment to be made whether or not the routes are desirable routes for passing the endoscope and the routes may be prioritized based on the scores. For example, it is conceivable that, based on a bent angle of a branch portion of a route, scores are set such that a lower priority is given to a route if it includes a largely bent portion in the middle. Further, for example, scores may be set such that the longer the route, the lower the priority. Still further, scores from a plurality of viewpoints may be weight added and a route may be prioritized based on the added score.

Still further, priority may be provided with respect to each route which includes each target point based on a further score calculated through weight addition of a score of a target point and a score with respect to each route described above that includes each target point.

The each embodiment described above is illustrative purposes only, and all of the foregoing descriptions should not be used to interpret as limiting the technical scope of the present invention.

In addition, various modifications made to the system configurations, hardware configurations, processing flows, module organizations, user interfaces, specific processing contents, and the like of the embodiments described above without departing from the spirits of the present invention are included in the technical scope of the present invention.

The image processing apparatus 3 may have a configuration in which the function as each unit described above is shared by a plurality of computers. Further, any known components may be employed as the components constituting the system, such as the input unit, display, and the like.

What is claimed is:

1. An image processing apparatus, comprising:
   one or more hardware processors configured to implement:
      a tubular structure extraction unit that extracts, from volume data captured by imaging a region of a subject which includes a tree-shaped tubular structure, the tubular structure;
      a target region setting unit that determines a target region which should be reached by an endoscope through the tubular structure in the volume data;
      a target point extraction unit that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and
      a route determination unit that identifies and determines a route of the tubular structure from a predetermined start point in the tubular structure to the extracted target point as a route through which the endoscope should be passed,
   wherein the second condition is changed in the reference angle according to the diameter of the tubular structure such that the smaller the diameter of the tubular structure, the smaller the reference angle, and
   wherein, in the second condition, if the diameter of the tubular structure is greater than or equal to the diameter of the endoscope multiplied by a given factor which is greater than or equal to 1, a first reference angle is used as the reference angle, while if the diameter of the tubular structure is smaller than the diameter of the endoscope multiplied by the given factor, a second reference angle which is smaller than the first reference angle is used as the reference angle.

2. The image processing apparatus of claim 1, wherein the given factor is in the range of 1 to 1.5.

3. The image processing apparatus of claim 1, wherein the second reference angle is less than or equal to an angle 2.5 degrees greater than a half angle of view of the endoscope.

4. The image processing apparatus of claim 1, wherein the target point extraction unit takes the target point as a point further satisfies a fourth condition that a portion of the tubular structure where the point is located does not belong to a given portion of the tubular structure where damage should be avoided.

5. The image processing apparatus of claim 1, wherein the target point extraction unit takes the target point as a point further satisfies a fifth condition that there is no obstacle between the point and the target region.

6. The image processing apparatus of claim 1, wherein the target point extraction unit identifies, among a plurality of divided sections of the tubular structure, a section closest to the target region and extracts the target point only in the identified section.

7. The image processing apparatus of claim 1, wherein the tubular structure is a bronchus.

8. The image processing apparatus of claim 1, wherein the point in the target region is either a center of gravity or a center of the target region.

9. The image processing apparatus of claim 1, wherein the point in the target region is either a first point of the target region or a second point of the target region,
   wherein a largest judgement angle is formed by the first point, and
   wherein a smallest judgement angle is formed by the second point.

10. An image processing apparatus, comprising:
    one or more hardware processors configured to implement:
       a tubular structure extraction unit that extracts, from volume data captured by imaging a region of a subject which includes a tree-shaped tubular structure, the tubular structure;
       a target region setting unit that determines a target region which should be reached by an endoscope through the tubular structure in the volume data;
       a target point extraction unit that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and
       a route determination unit that identifies and determines a route of the tubular structure from a predetermined start point in the tubular structure to the extracted target point as a route through which the endoscope should be passed,
    wherein the target point extraction unit takes the target point as a point that further satisfies a third condition that the diameter of a portion of the tubular structure where the point is located is less than a given threshold value.

11. An image processing method to be performed by an image processing apparatus, the method comprising:
    a tubular structure extraction step that extracts, from volume data captured by imaging a region of a subject which includes a tree-shaped tubular structure, the tubular structure;
    a target region setting step that determines a target region which should be reached by an endoscope through the tubular structure in the volume data;

a target point extraction step that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and a route determination step that identifies and determines a route of the tubular structure from a predetermined start point in the tubular structure to the extracted target point as a route through which the endoscope should be passed, wherein the second condition is changed in the reference angle according to the diameter of the tubular structure such that the smaller the diameter of the tubular structure, the smaller the reference angle, and wherein, in the second condition, if the diameter of the tubular structure is greater than or equal to the diameter of the endoscope multiplied by a given factor which is greater than or equal to 1, a first reference angle is used as the reference angle, while if the diameter of the tubular structure is smaller than the diameter of the endoscope multiplied by the given factor, a second reference angle which is smaller than the first reference angle is used as the reference angle.

12. A non-transitory computer readable recording medium containing an image processing program that causes a computer to perform:

a tubular structure extraction step that extracts, from volume data captured by imaging a region of a subject which includes a tree-shaped tubular structure, the tubular structure;

a target region setting step that determines a target region which should be reached by an endoscope through the tubular structure in the volume data;

a target point extraction step that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and a route determination step that identifies and determines a route of the tubular structure from a predetermined start point in the tubular structure to the extracted target point as a route through which the endoscope should be passed, wherein the second condition is changed in the reference angle according to the diameter of the tubular structure such that the smaller the diameter of the tubular structure, the smaller the reference angle, and wherein, in the second condition, if the diameter of the tubular structure is greater than or equal to the diameter of the endoscope multiplied by a given factor which is greater than or equal to 1, a first reference angle is used as the reference angle, while if the diameter of the tubular structure is smaller than the diameter of the endoscope multiplied by the given factor, a second reference angle which is smaller than the first reference angle is used as the reference angle.

13. An image processing method to be performed by an image processing apparatus, the method comprising:

a tubular structure extraction step that extracts, from volume data captured by imaging a region of a subject which includes a tree-shaped tubular structure, the tubular structure;

a target region setting step that determines a target region which should be reached by an endoscope through the tubular structure in the volume data;

a target point extraction step that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and a route determination step that identifies and determines a route of the tubular structure from a predetermined start point in the tubular structure to the extracted target point as a route through which the endoscope should be passed, wherein the target point is taken as a point that further satisfies a third condition that the diameter of a portion of the tubular structure where the point is located is less than a given threshold value.

14. A non-transitory computer readable recording medium containing an image processing program that causes a computer to perform:

a tubular structure extraction step that extracts, from volume data captured by imaging a region of a subject which includes a tree-shaped tubular structure, the tubular structure;

a target region setting step that determines a target region which should be reached by an endoscope through the tubular structure in the volume data;

a target point extraction step that extracts, among points on a route of the tubular structure, a point by determining that the point satisfies a first condition that the point on the route is located within a given range from the target region and a second condition that a judgement angle, which is an angle formed between a direction from the point on the route to a point in the target region and a direction in which the route of the tubular structure is determined to extend from the point on the route, is less than or equal to a reference angle which is at least a given acute angle, as a target point that should be reached by a distal end portion of the endoscope; and a route determination step that identifies and determines a route of the tubular structure from a predetermined start point in the tubular structure to the extracted target point as a route through which the endoscope should be passed, wherein the target point is taken as a point that further satisfies a third condition that the diameter of a portion of the tubular structure where the point is located is less than a given threshold value.

* * * * *